US011662277B2

United States Patent
Cuypers et al.

(10) Patent No.: US 11,662,277 B2
(45) Date of Patent: May 30, 2023

(54) METHOD AND APPARATUS FOR DEMOLDING AND ANALYZING A DIRECT ANALYSIS SAMPLE

(71) Applicant: HERAEUS ELECTRO-NITE INTERNATIONAL N.V., Houthalen (BE)

(72) Inventors: Jan Cuypers, Houthalen (BE); Jean-Paul Verhoeven, Houthalen (BE)

(73) Assignee: HERAEUS ELECTRO-NITE INTERNATIONAL N.V., Houthalen (BE)

( * ) Notice: Subject to any disclaimer, the term of this patent is extended or adjusted under 35 U.S.C. 154(b) by 118 days.

(21) Appl. No.: 16/776,219

(22) Filed: Jan. 29, 2020

(65) Prior Publication Data
US 2020/0256768 A1    Aug. 13, 2020

(30) Foreign Application Priority Data
Feb. 11, 2019 (EP) ..................... 19156339

(51) Int. Cl.
*G01N 1/12* (2006.01)
*G01N 33/2025* (2019.01)
*G01N 33/205* (2019.01)

(52) U.S. Cl.
CPC ........... *G01N 1/125* (2013.01); *G01N 33/205* (2019.01); *G01N 33/2025* (2019.01)

(58) Field of Classification Search
CPC ... G01N 1/125; G01N 33/2025; G01N 33/205
(Continued)

(56) References Cited

U.S. PATENT DOCUMENTS 3,996,803 A    12/1976  Falk
6,433,862 B1   8/2002   Schock et al.

FOREIGN PATENT DOCUMENTS

CA    2757559       *  6/2012
CN    204286857 U      4/2015
(Continued)

OTHER PUBLICATIONS

Kobesen et al. The changing face of analytical production control at Hoogovens, Ijumuiden, 42nd Chemists' Conference Proceedings, 1989, pp. 17-21.

*Primary Examiner* — Robert R Raevis
(74) *Attorney, Agent, or Firm* — Blank Rome LLP

(57) ABSTRACT

The present invention relates to an apparatus for demolding and analyzing a direct analysis sample formed from a molten metal material contained within a sample chamber assembly, wherein the sample chamber assembly comprises at least a sample housing, a cover plate and closing means, comprising:
  a cabinet defining an interior and comprising at least one opening for the sample housing to enter the cabinet, and analyzing means located inside the cabinet for analyzing an analysis surface of the sample;
  demolding means adapted to remove at least the closing means to expose at least part of the analysis surface of the sample; and
  transporting means adapted to hold and transport the sample housing at least between a sample demolding position, where the closing means is removed by the demolding means, and a sample analysis position, where the analysis surface of the sample is analyzed by the analyzing means, and wherein the sample demolding position and the sample analysis position are different from each other.

(Continued)

The invention also relates to a system and method for demolding and analyzing a direct analysis sample.

20 Claims, 9 Drawing Sheets

(58) Field of Classification Search
USPC .............. 73/864.31, 864.53–864.59, 864.81, 73/864.83, 864.84; 356/300–334, 237.2, 356/237.3, 256; 250/306, 307; 266/274–276, 80, 99, 100
See application file for complete search history.

(56) References Cited

FOREIGN PATENT DOCUMENTS

| | | | |
|---|---|---|---|
| DE | 19852528 | A1 | 5/2000 |
| EP | 2626685 | A1 | 8/2013 |
| EP | 3336511 | A1 | 6/2018 |
| EP | 3336512 | A1 | 6/2018 |
| EP | 3336513 | A1 | 6/2018 |
| EP | 3336514 | A1 | 6/2018 |
| GB | 1008829 | A | 11/1965 |
| JP | 2001153760 | * | 6/2001 |
| JP | 2001153760 | A | 6/2001 |
| JP | 2004012336 | * | 1/2004 |
| WO | 2016204683 | * | 12/2016 |

* cited by examiner

METHOD AND APPARATUS FOR DEMOLDING AND ANALYZING A DIRECT ANALYSIS SAMPLE

CROSS REFERENCE TO RELATED APPLICATION

This application claims the benefit of European Application No. 19156339.4 filed Feb. 11, 2019, the entire contents of which are incorporated herein by reference.

FIELD OF THE INVENTION

The invention relates to a method and apparatus for demolding and analyzing a direct analysis sample formed from a molten metal material contained within a sample chamber assembly, wherein the sample chamber assembly comprises at least a sample housing, a cover plate and closing means. The invention also relates to a system comprising an apparatus and a direct analysis sample.

BACKGROUND OF THE INVENTION

During the metallurgical processing of iron and steel, the molten metal material is sometimes mixed with other molten metal batches or treated to alter its chemistry prior to being charged into a converter. Accordingly, it is advantageous to extract a sample of the molten metal material to determine its chemical composition during treatment and for use in mass and energy balances of the converter process and for process control during steelmaking processes. Devices for extracting samples for chemical analysis are well known in the art. An example of one such prior art reference is U.S. Pat. No. 3,996,803.

Typically, a conventional molten metal or steel sampler is a low-cost sampling device arranged in a refractory body and mounted on a carrier tube and having an inlet for the molten metal to enter a chamber that is formed by two thick metal chill plates. Conventional samples have a temperature of about 500° C. to 800° C. when they are being retrieved from the molten metal and need cooling before the samples can be analyzed. Also, the analysis surfaces of conventional samples need to be prepared by grinding prior to analysis to remove oxides from the surfaces and to provide the required flat topography.

Whereas, a newly developed type of molten metal immersion samplers, commonly referred to as direct analysis (DA) samplers do not require any kind of cooling, the typical sample temperature is only around 100° C., ranging from 70° C. to 130° C., when retrieved from the molten metal bath. In addition, direct analysis samples do not require surface preparation before they are being analyzed, which results in an economic benefit both in terms of the availability of analyses results as well as in laboratory time savings.

For example, prior art references EP3336513A1, EP3336514A1, EP3336512A1, and EP3336511A1 relate to direct analysis samplers that do not require any sample preparation steps, such as cooling, cleaning and grinding. Once the sample chamber assembly containing the sample is retrieved from the molten metal, a part of the sample chamber assembly, such as the cover plate, can be removed to expose at least part of an analysis surface of the sample, which can be immediately analyzed.

The composition of a sample can be determined using an analysis instrument comprising arc spark-optical emission spectroscopy equipment, also sometimes just referred to as optical emission spectroscopy or OES on the analysis surface of the sample. Optical emission spectroscopy systems are generally the most effective systems for determining the chemical composition of a sample comprising metal and for controlling the processing of molten metals due to their rapid analysis times and inherent accuracy. Thus, optical emission spectroscopy analysis is typically used during molten metal processes for controlling the progress of molten metal production.

When a sample chamber assembly is opened manually to expose the analysis surface, there is a high risk that the analysis surface will get contaminated. The deviations of the elements to be analyzed are mainly caused by the displacement of the cover plate. In particular, deviations on aluminum and deviations on carbon and sulfur can be observed. Deviations on aluminum are generally caused by mechanically contacting the cover plate and the analysis surface. The deviations on carbon and sulfur are caused by a more severe displacement so that part of the sealing material used to seal the space between sample housing and the cover plate touches the analysis surface of the sample before the sample chamber assembly is opened. Also, dirt particles and tar deposits originating from the refractory body can be another source of contamination. In addition, the handling of the sample chamber assemblies after demolding can be yet another source of contamination. The handling is typically done by mechanical tools, handled by a glove wearing operator. Therefore, it is intended to eliminate or at least reduce the adverse effects of contamination on the analysis results. Some analyses, such as for example end blow analyses in the Basic Oxygen Process or in the Electric Arc Furnace require an analysis accuracy in the range of a few ppm.

Apparatuses for automatically demolding samples formed from a molten metal are already known in the prior art. For example, prior art reference EP2626685A1 describes a spinner device for spinning a sample contained in a sample housing against an impact element for demolding the sample. Prior art reference DE19852528A1 describes a cutting device which is adapted to cut a sample contained in a housing in half for demolding the sample.

However, the apparatuses known from the prior art are not suitable for demolding a direct analysis sample without contaminating or destroying the analysis surface during the demolding process. Consequently, the analysis surfaces of the prior art samples are often contaminated with dirt particles that can contaminate the analysis instrument and can cause incorrect analysis results.

Therefore, there still exists a need for an improved apparatus and technique for demolding and analyzing a direct analysis sample formed from a molten metal material contained within a sample chamber assembly where the analysis surface of the sample is kept clean and is not subject to major contamination when the sample chamber assembly is opened to expose the analysis surface.

This need is fulfilled by the subject-matter of the independent claims.

SUMMARY OF THE INVENTION

The invention provides an apparatus for demolding and analyzing a direct analysis sample formed from a molten metal material contained within a sample chamber assembly, wherein the sample chamber assembly comprises at least a sample housing, a cover plate and closing means, comprising:

a cabinet defining an interior and comprising at least one opening for the sample housing to enter the cabinet, and analyzing means located inside the cabinet for analyzing an analysis surface of the sample;

demolding means adapted to remove at least the closing means to expose at least part of the analysis surface of the sample; and transporting means adapted to hold and transport the sample housing at least between a sample demolding position, where the closing means is removed by the demolding means, and a sample analysis position, where the analysis surface of the sample is analyzed by the analyzing means, and wherein the sample demolding position and the sample analysis position are different from each other.

For example, the sample chamber assembly can be one of the sample chamber assemblies described in EP3336513A1, EP3336514A1, EP3336512A1, and/or EP3336511A1.

The sample chamber assembly can be made of a material which is a good thermal conductor, such as copper or aluminum. The cover plate, which can also be referred to as lid, can be made from the same material as the sample housing or from a different material such as fused silica or a refractory ceramic material. The cover plate can have the same width and length as the sample housing and can have a first side and an opposing second side. The first side of the cover plate can face the sample housing in an assembled position. A sealing member can be additionally provided on the first face of the cover plate to be positioned between the sample housing and the cover plate in the assembled configuration of the sample chamber assembly to provide a gas tight seal. The sealing member can be a gasket formed of paper, silicone or any similar polymer and can be dimensioned to encompass or surround a ridge in the assembled configuration of the sample chamber assembly.

In the assembled configuration of the sample chamber assembly, at least the cover plate and the sample housing are assembled together to form the sample cavity, while being held together by the closing means, for example a clamp, brace, spring or clip with a compression force sufficiently high to withstand the pressure of purge gas applied prior to filling the sample cavity and to resist a tendency of the sample housing and cover plate to separate due to the force of molten metal flowing into the sample housing and filling the sample cavity.

When the sample cavity is filled with molten metal, the molten metal freezes against the first side of the cover plate, thereby forming the analysis surface of the direct analysis sample, which is the surface to be analyzed after demolding the sample.

The term "cabinet" can be used to refer to an enclosure of at least the analyzing means that shields the analyzing means and reduces or prevents exposure of the analyzing means to dust and dirt particles. The cabinet can have doors for ease of maintenance and can be foreseen with acclimatization, e.g. cooling and heating, means. Also, the cabinet comprises an opening for the sample housing to enter the cabinet space by means of the transporting means. During stand-by operation at least part of the transporting means can be positioned in the opening to reduce the risk of dust and dirt particles entering the cabinet.

The term "transporting means" adapted to hold and transport the sample housing can be used to refer to a mechanism that holds the sample housing, preferably by clamping the sample housing between two clamps, and that transports the held sample housing towards the inside of the cabinet for analyzing the exposed analysis surface. In addition, the "transporting means" can be also adapted to discard the sample housing after the analysis, for example by opening one clamp or both clamps so that the sample housing can fall into a collection bin.

The sample demolding position can be a position outside the cabinet in which the closing means is removed, and the analysis surface is exposed. In one example, the demolding position can be the same position as an inserting position where the sample housing is inserted into the transporting means. In an alternative example, the demolding position and the inserting position can be different positions where the sample chamber assembly or at least the sample housing is transported between the inserting position, the demolding position, and the analysis position.

The transporting means can be realized with at least two clamps or brackets that are mounted on a slider system such as a glide surface/track or a slide cam which allows the clamps to slide along a predetermined path of the slider system. The transporting means can, for example, comprise an actuator for detecting the presence of the sample housing which can be a spring-loaded mechanism or an electronic sensor that causes a relative movement of the two clamps to hold the sample housing. The transporting means can hold the sample housing during demolding to expose at least part of the analysis surface of the sample and transporting the sample housing towards and into the sealed cabinet in which the analyzing means are located for analyzing the analysis surface.

The term "demolding means" adapted to remove at least the closing means to expose at least part of the analysis surface of the sample can be used to refer to a mechanism that is adapted to automatically remove the closing means. In one example, the demolding means can also penetrate the sample chamber assembly, e.g. remove or displace some of the material of the sample chamber assembly, such as for example the cover plate, to expose at least part of an analysis surface of the sample. For example, the demolding means can be realized by a blade, pin, rod, piston, or by any suitable device that can be used to remove the closing means, and/or the cover plate. For example, the demolding means can further comprise a supporting surface on which the sample chamber assembly can be arranged with its cover plate facing the supporting surface and being in contact with the supporting surface. Once the closing means, e.g. a clamp, got removed and while the sample housing is still held by the transporting means, the supporting means can be retracted in a backward/forward, sideways, or downwards direction to allow the cover plate to come off by means of gravity so that it can preferably fall into a collection bin located underneath. Alternatively, or in addition the demolding means could further comprise another blade pin, rod, piston, etc. to mechanically remove the cover plate.

Advantageously, removal of the cover plate takes place without mechanically contacting the analysis surface, but instead by lifting the cover plate away from the analysis surface or letting it separate by itself once the closing means was removed. Hence, removal of the cover plate does not cause abrasion or friction to the analysis surface of the sample.

In an example, the transporting means can comprise an abutment surface, preferably arranged at least in part parallel to the second clamp, to prevent movement of the sample housing in a sideways direction.

For example, the abutment surface can be rigidly arranged, wherein the distance between abutment surface and first clamp and/or second clamp can be chosen to match the width of the sample housing. Advantageously, by means of the abutment surface, the sample chamber assembly can be more easily positioned into the apparatus.

Advantageously, the invention provides an apparatus that allows demolding and analyzing a sample in a fast and efficient way with a greatly reduced risk of contamination of the sample's analysis surface. Also, the time between taking the sample and analyzing the sample can be greatly reduced compared to the techniques known from the prior art.

In an example, the demolding means comprises at least one blade arranged, preferably movably arranged, in at least a sideways direction or a longitudinal direction relative to an axis formed by the demolding position and the analysis position and adapted:
  (i) to move over a surface of the sample chamber assembly to remove the closing means of the sample chamber assembly, preferably a clamp or a brace, holding the sample housing and the cover plate together, or
  (ii) to move over a surface of the sample chamber assembly to remove the closing means and to penetrate the sample chamber assembly, preferably at a location between the sample housing and the cover plate to remove the cover plate from the sample housing, to expose at least part of the analysis surface of the sample.

Here, the term "sideways direction" can be used to refer to a direction perpendicularly to the direction of movement of the transporting means, wherein the transporting means can move at least between the sample demolding position and the sample analysis position. The term "longitudinal direction" can be used to refer to a direction of movement on an imaginary line between the sample demolding position and the sample analysis position in the direction of movement of the transporting means.

For demolding, the blade can directly move over the surface of the sample housing or with a distance between blade and surface of the sample housing to get hold of at least part of the closing means and to remove it from the sample housing while the blade moves. Additionally, the blade or another blade associated with the blade can also penetrate the sample chamber assembly, such as moving into the material of the sample chamber assembly to separate at least part of the sample chamber assembly to expose the analysis surface.

Advantageously, demolding can be performed automatically without any interference by the operator.

In one example, the demolding means comprises at least one supporting surface to support at least a part of the cover plate of the sample chamber assembly when being held by the sample transporting means and wherein the supporting surface is movably arranged to allow the cover plate to separate from the sample housing by means of gravitational force.

The supporting surface can be a surface on which the sample chamber assembly rests when the sample chamber assembly is held for removing the closing means. The sample chamber assembly can be loaded such that the cover plate of the sample chamber assembly is placed on the supporting surface. Once the closing means is removed, the supporting surface can be removed, for example by lifting, sliding or pivoting it away, so that the cover plate can fall off to expose the analysis surface. Therefore, the supporting surface being movably arranged can be understood as movably arranged relative to the sample chamber assembly held by the transporting means.

In one example, the transporting means comprises: a first clamp and a second clamp for holding the sample housing and to stop movement of the sample housing in at least a forward and a backward direction from both the demolding position and analysis position, wherein the first clamp and the second clamp are movably arranged in the forward and backward direction for transporting the sample housing between the sample demolding position and the sample analysis position, wherein the second clamp is arranged at least in part opposite the first clamp, preferably the first clamp or the second clamp further comprises sensor means for detecting contact of the first clamp or the second clamp and the sample housing.

As already described above, the two clamps can be mounted on a slider system such as a glide surface/track or a slide cam which allows the clamps to slide along the way of the slider system. The slider system can extend from the inserting position, e.g. a sample bay, where the sample chamber assembly can be positioned by an operator into a space between the first clamp and the second clamp to the analysis means where the analysis surface of the sample is analyzed. Here, the terms "forward and backward direction" can be used to refer to a forward and backward direction along the axis extending from the sample bay to the analysis means.

The first clamp and the second clamp can be moved on the slider system independently from each other or can be moved together, e.g. in case the first clamp and the second clamp are produced from one piece of material. In examples of the invention, the first and second clamp can be moved by hand, by a mechanism, or a drive, such as for example an electric or pneumatic drive or motor. In one example of the invention, the first clamp located closer to the analyzing means than the second clamp comprises sensor means, such as a contact or proximity sensor, alternatively a mechanical spring biased mechanism can be employed, that can detect a sample housing being placed between the first clamp and the second clamp. Upon detecting the sample housing between the first clamp and the second clamp, at least one of the clamps or both clamps can move towards each other to hold the sample housing, and/or locking means can be employed to hold the sample housing.

In one example, the second clamp comprises locking means, preferably a spring biased latch, adapted to allow the sample housing to be moved past the locking means towards the first clamp, and to prevent movement of the sample housing in the opposite direction, preferably the first clamp comprises another locking means, preferably another spring biased latch, adapted to prevent movement of the sample housing in the forward and backward direction.

The locking means can be arranged on a side surface of the second clamp facing the first clamp, wherein the locking means can comprise a latch such as a toggle lever or rocker lever that allows to move the sample housing towards the first clamp in at least a horizontal plane and when the sample housing is moved past the locking means, a spring or an actuator in the locking means can activate the lever such that the sample housing is locked and cannot be moved back anymore. In one example, where an actuator is used, triggering means of the actuator could be coupled to the sensor means as described in the previous example. Upon detecting the presence of a sample housing between the first clamp and the second clamp, the triggering means could cause the actuator to lock the lever such that the sample housing is locked between the first clamp and the second clamp. Alternatively, a spring which is compressed by retracting the lever while the sample housing is moved past the lever could expand again for moving the lever out again so that the sample housing is locked between the first clamp and the second clamp.

Alternatively, or additionally, the locking means could also be arranged to prevent movement of the sample housing in each spatial direction.

Advantageously, the locking means allow to easily load a sample chamber assembly into the apparatus and to reliably hold and transport the sample housing during demolding and analyzing.

In another example, the transporting means comprises at least one drive means, preferably an electric motor, to move the first clamp and the second clamp comprising the locking means and holding the sample housing in the forward direction towards the analyzing means, preferably the transporting means comprises a first drive means for moving the first clamp and a second drive means for moving the second clamp independently from each other.

The clamps can be movable, for example on a glide surface/track or a slide cam, by means of a drive means which could be an electric motor, a mechanical system activatable by manual force, or a pneumatic system.

In an example, the demolding means comprises actuation means for moving, preferably sequentially moving, the blade and the supporting surface, and wherein the actuation means comprises a hand gear for moving the blade and the supporting surface mechanically, or a push rod for moving the blade and the supporting surface pneumatically or electrically, between a first and a second position.

In another example, the actuation means is adapted to be moved between a first and a second position, wherein:

in the first position, the actuation means and blade are arranged for loading the sample housing, wherein at least the first clamp is at least partly arranged in the opening of the sealed cabinet, and in the second position, the actuation means and blade are arranged for analyzing the sample by the analyzing means, wherein at least the second clamp is at least partly arranged in the opening of the sealed cabinet.

The actuation means are adapted to be moved between the first and the second position, wherein in the first position the actuation means is arranged for loading the sample housing, wherein at least the first clamp is at least partly arranged in the opening of the sealed cabinet. In the first position, the sample housing can be put between the first and second clamps.

Moving the actuation means causes at least the demolding means to remove the closing means. The movement also causes the supporting surface to be removed at the same time or shortly after, or the movement causes the blade to penetrate the sample chamber assembly, preferably at a location between the sampling housing and the cover plate for exposing at least part of the analysis surface of the sample.

In the second position, the actuation means is arranged for analyzing the sample by the analyzing means, wherein at least the second clamp is at least partly arranged in the opening of the sealed cabinet. In the second position, the demolded sample housing can be transported by means of the first and second clamp to the inside of the cabinet for analysis, while at least the second clamp is at least partly arranged in the opening of the cabinet. For example, the first and second clamp are both moved towards the inside of the cabinet, wherein the first clamp is moved past the analyzing means to position the analysis surface on top of the analyzing means, and the second clamp is moved into the opening holding the sample housing together with the first clamp.

Advantageously, arranging either the first clamp or the second clamp in the opening of the cabinet in one of the two positions allows to reduce the number of unwanted particles, such as dust, entering the cabinet, which could falsify the analysis results.

In another example, at least a first dust cover mounted on a stationary part of the apparatus, and a second dust cover mounted on the blade or a movable part mechanically associated with the blade and moving together with the blade, wherein at least part of the first dust cover and the second dust covers are arranged to be spaced apart to allow loading the sample chamber assembly when the actuation means is in the first position, and at least partly overlap when the actuation means is in the second position, preferably at least one dust seal such as a brush seal is arranged on one of the first and/or second dust covers to seal a remaining space between the first and second dust cover when they are overlapping.

Advantageously, by employing the first and second dust cover the number of unwanted particles, such as dust, entering the sealed cabinet can be further reduced.

In an example thereof, the first dust cover comprises an insertion-opening for inserting the sample chamber assembly into the transporting means, and wherein the second dust cover overlaps the insertion-opening when the actuation means is in the second position.

In another example, the analyzing means comprise an optical emission spectrometer, preferably a spark optical emission spectrometer, more preferably a top-loaded optical emission spectrometer comprising a spring to hold the analysis surface of the sample at a distance to a contact electrode of the optical emission spectrometer, and adapted to establish an electric contact to the analysis surface of the sample when the spring is in a compressed state, most preferably a top-loaded optical emission spectrometer comprising a spring having a force of less than 100 Newton, preferably less than 10 Newton to hold the analysis surface at a distance of preferably less than 1 mm to the contact electrode of the optical emission spectrometer.

Optical emission spectroscopy involves exciting atoms of a target sample of which knowledge of the composition is desired and examining the wavelength of photons emitted by atoms during transition from an excited state to a lower energy state. Each element in the periodic table emits a characteristic set of discrete wavelengths when its atoms return from an excited state to a lower energy state. By detecting and analyzing these wavelengths, the elemental composition of a sample can be determined in accordance with a calibration curve, thereby showing the relationship between the spectral intensity ratio and the concentration of the element in the standard sample.

The spectral light may be produced by irradiation with electromagnetic radiation, such as by a laser or x-rays, but is generally produced for optical emission spectroscopy by a short spark produced by a spark generator incident upon the target of which knowledge of its elemental composition is desired. In this case, the target is the sample, in particular the analysis surface of the sample. Spark generators, their intensity and their pulse regime vary according to the specific optical emission spectroscopy equipment. Irrespective of the spark energy input, the accuracy and reliability of such optical emission spectrometers has been known to be dependent on the accuracy and quality of the detector and optics used to receive the radiation emitted from the sample and the homogeneity of the sample itself.

The optical emission spectroscopy analysis procedure begins with the conductive sample being positioned with its analysis surface face down on a predetermined region of the stage of the analysis instrument, namely an optical emission spectrometer. More particularly, the sample is positioned so as to span and close the analysis opening of the spectrometer and an anode nearly abuts the analysis surface of the sample. Once the desired positioning of the sample and proximity of the anode and analysis surface is achieved, a spark is discharged between the anode, which is often referred to as contact electrode, and the conductive metal sample which is electrically connected to the spectrometer stage. This connection is, in most cases, made by gravitational force in combination with a small load, e.g. a push rod. An optical detector receives the emitted light from the excavated material of the analysis surface. The spark chamber, formed in part by the space between the anode and the sample, can be continuously purged with argon or other inert gas to avoid air ingress which would lead to erroneous analysis values.

In an example, the apparatus comprises means to apply a purge gas to the analysis surface of the sample for removing loosely attached particles.

For example, the means to apply a purge gas can comprise a gas nozzle arranged between the demolding position and the analysis position. In one example, the gas nozzle can be arranged inside the cabinet at the opening for the sample housing to enter the cabinet and can further be adapted to apply a short gas purge to the analysis surface of the sample when the sample housing is moved past the gas nozzle to remove loosely attached particles from the sample.

The invention also relates to a system for demolding and analyzing a direct analysis sample comprising:

an apparatus according to any of the preceding claims; and a direct analysis sample formed from a molten metal material contained within a sample chamber assembly and comprising at least a sample housing, a cover plate and closing means, wherein a ratio of a mass of the sample housing to a mass of the molten metal solidified in the sample housing is higher than 5, preferably higher than 9.

Also, the invention relates to a method for demolding and analyzing a direct analysis sample formed from a molten metal material within a sample chamber assembly and comprising at least a sample housing, a cover plate and closing means, comprising the steps: holding and transporting the sample housing at least between a sample demolding position and an analyzing position, wherein the sample demolding position and the sample analysis position are different from each other;

removing the closing means to expose at least part of an analysis surface of the sample in the sample demolding position; and analyzing the analysis surface of the sample in the analysis position by analyzing means located inside a cabinet after transporting the sample housing from the demolding position through an opening in the cabinet into the analysis position.

In an example, the step of holding and transporting comprises:

holding the sample housing between a first clamp and a second clamp to stop movement of the sample housing in at least a forward and backward direction.

In an example, the step of removing the closing means comprises:

moving at least one movably arranged blade in at least a sideways direction or a longitudinal direction relative to the first and second clamp:

(i) over a surface of the sample chamber assembly to remove the closing means of the sample chamber assembly, preferably a clamp or a brace, holding the sample housing and the cover plate together, or (ii) over a surface of the sample chamber assembly to remove the closing means and to penetrate the sample chamber assembly, preferably at a location between the sample housing and the cover plate, to remove the cover plate from the sample housing, to expose at least part of the analysis surface of the sample, and moving a supporting surface in at least the sideways direction to allow the cover plate to separate from the sample housing by means of gravitational force.

In another example, the step of holding and transporting the sample housing comprises: holding and transporting the sample housing, after removing the closing means and cover plate, with the analysis surface of the sample spaced from surrounding objects such that the analysis surface of the sample is held and transported contact, abrasion and/or friction free.

BRIEF DESCRIPTION OF THE DRAWINGS

The following schematic drawings show aspects of the invention for improving the understanding of the invention in connection with some exemplary illustrations, wherein.

DETAILED DESCRIPTION

Figure 1A:
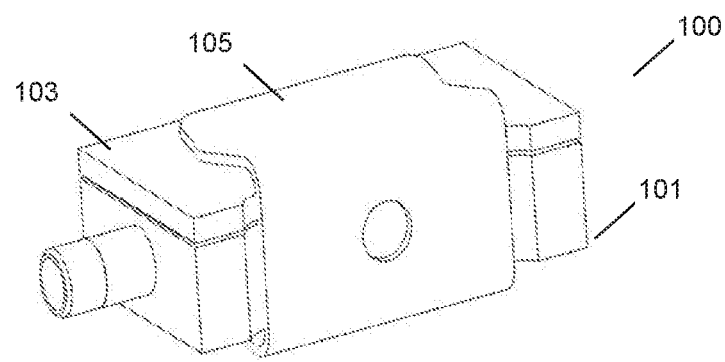
FIGS. 1a-1c show schematic views of a sample chamber assembly.

The sample chamber assembly 100 which is shown in FIG. 1a comprises a sample housing 101, a cover plate 103 and closing means 105.

In the shown embodiment, the cover plate 103 has the same width and length as the sample housing 101 and forms together with the sample housing 101, the sample cavity, while being held together by the closing means 105, which is shown as a clamp in FIG. 1a. The closing means 105 has a compression force sufficiently high to resist a tendency of the sample housing 101 and cover plate 103 to separate due to the force of molten metal flowing into the sample housing 101 and filling the sample cavity.

Figure 1B:
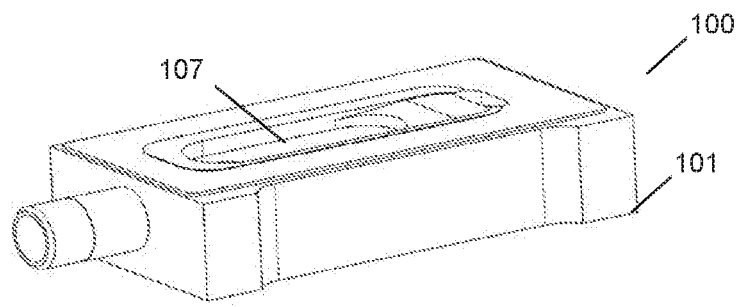

FIG. 1b shows the sample chamber assembly 100 of FIG. 1a having the cover plate and clamp removed. In the shown example, at least the part of the sample cavity 107 that is formed in the sample housing 101 can be seen.

Figure 1C:
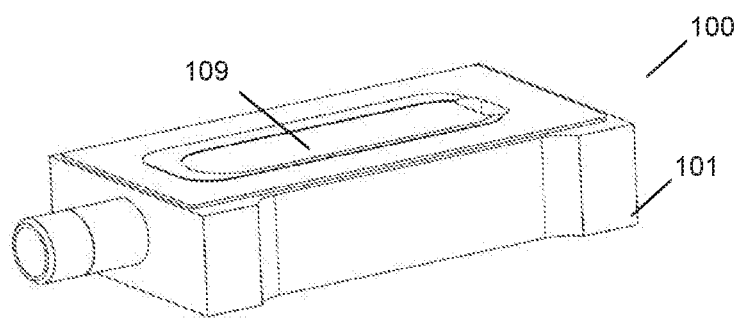

The sample chamber assembly 100 shown in FIG. 1c can be the sample chamber assembly of any of the preceding FIGS. 1a and/or 1b. However, the sample cavity is filled with metal, which froze against the cover plate, and thereby formed the analysis surface 109 of the direct analysis sample, which is the surface that can be analyzed by the analyzing means.

Figure 2:
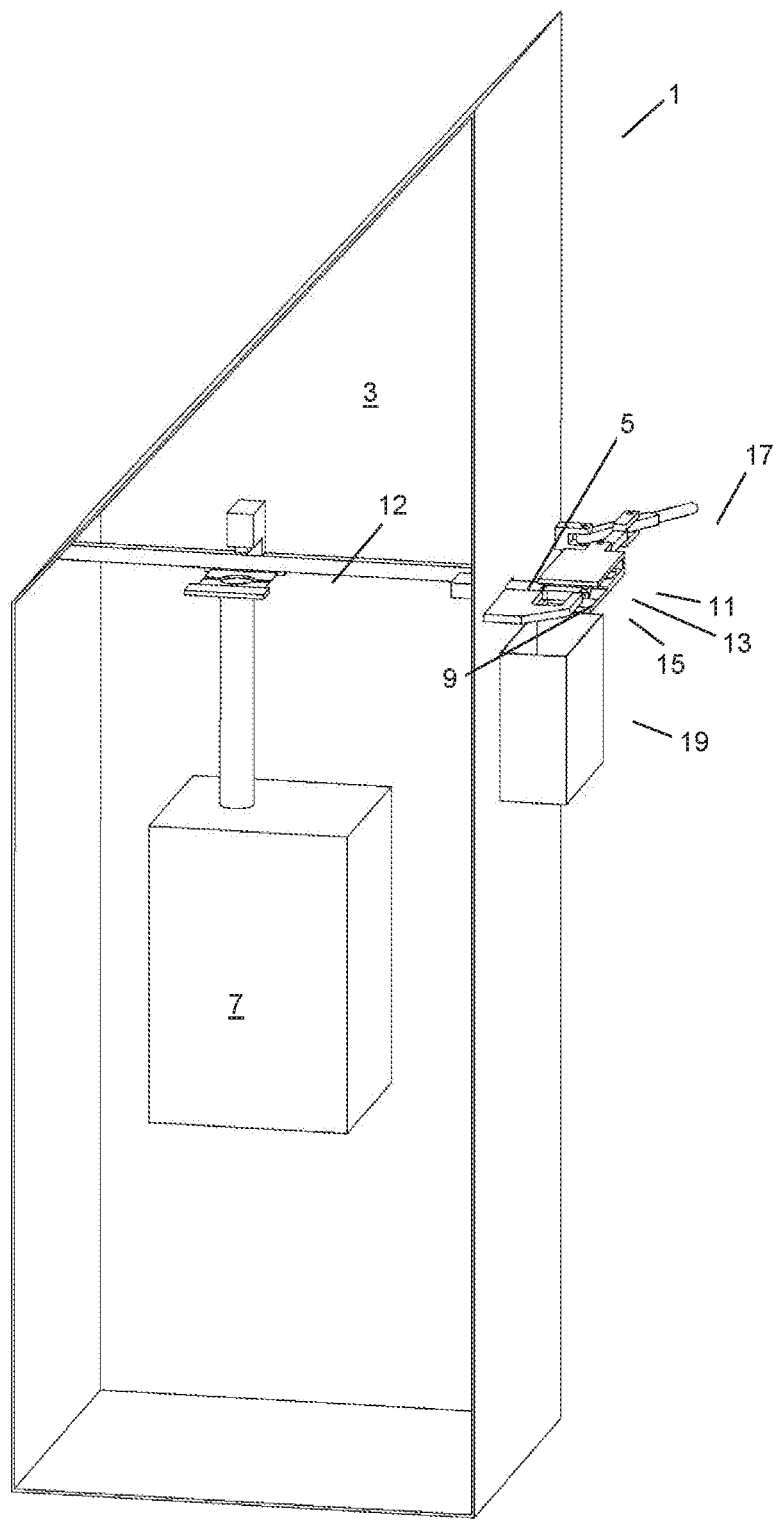
FIG. 2 shows a schematic view of an apparatus for demolding and analyzing a direct analysis sample according to an embodiment of the invention.

FIG. 2 shows a schematic view of an apparatus 1 for demolding and analyzing a direct analysis sample according to an embodiment of the invention.

Analyzing means 7 are located inside a cabinet 3 for analyzing the analysis surface of the sample. In the shown embodiment, the cabinet 3 has a rectangular ground section and a triangular top section and can be placed on the shop floor of a steel plant. In embodiments, not shown herein, the cabinet can have a different outer shape. The shown analyzing means 7 is realized in the shown embodiment by a top-loaded optical emission spectrometer. The cabinet 3 also comprises an opening 5 for the sample housing to enter the cabinet 3. The opening 5 can be arranged in the shell of the cabinet at a height convenient for an operator to place the sample chamber assembly into the apparatus 1.

The transporting means 9 are shown in FIG. 2 in a demolding position, wherein part of the transporting means 9 is arranged in the opening 5.

Also shown in FIG. 2 is a slider system 12 which comprises a glide surface/track or slide cam, and which allows the transporting means 9 to move on between the demolding position and an analysis position.

FIG. 2 further shows demolding means 11 for removing the closing means of the sample chamber assembly to expose the analysis surface of the sample. In the shown embodiment, the demolding means 11 comprises a blade 13, a supporting surface 15 and actuation means 17 which comprises in the shown embodiment a hand gear for moving the blade 13 and the supporting surface 15 between a first and a second position. Alternatively, in an embodiment not shown herein, the blade and the supporting surface can be also moved pneumatically or electrically. In the shown embodiment a collection bin 19 is arranged at the outside of the cabinet 3 for collecting the removed closing means and cover plates.

Figure 3A:
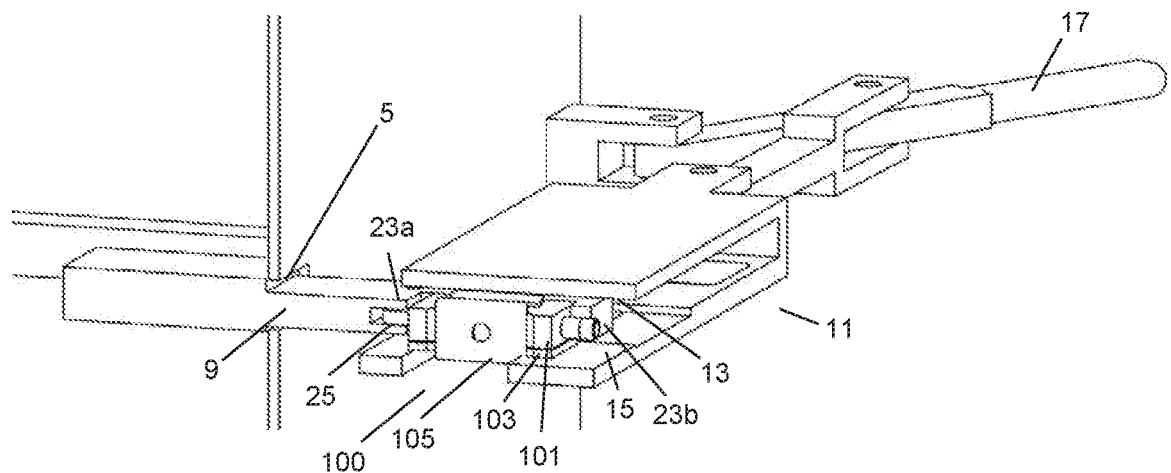
FIGS. 3a-3d show schematic views of the transporting means and the demolding means with the actuation means in a first position according to embodiments of the invention.
Figure 3B:
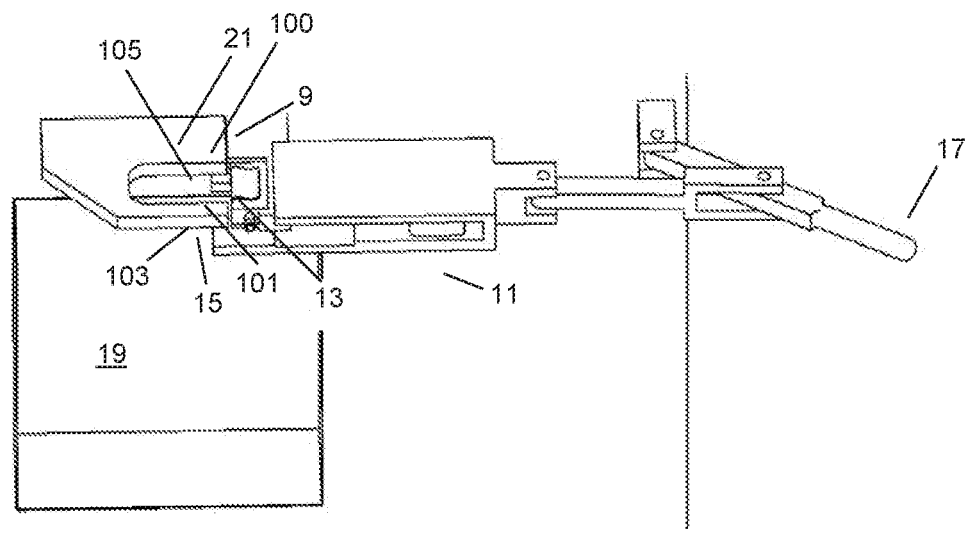

FIGS. 3a, 3b show schematic views of the transporting means 9 and the demolding means 11 with the actuation means 17 in a first position. In the shown embodiment the transporting means 9 comprises a first clamp 23a and a second clamp 23b that hold the sample housing 101 and stop movement of the sample housing 101 in a forward and a backward direction. Here, the term 'forward direction' can be defined by referring to transporting the sample housing 101 from the demolding position, in which it is shown in FIG. 3a, through the opening 5 into the cabinet 3. The term 'backward direction' can be defined by referring to the opposite direction. The first clamp 23a and the second clamp 23b that hold the sample housing 101 can also stop movement of the sample housing 101 in a sideways direction relative to the forward and backward direction.

In the shown embodiment the first clamp 23a and the second clamp 23b are movably arranged in the forward and backward direction for transporting the sample housing 101 between the sample demolding position and the sample analysis position. As shown in FIG. 3a, the first clamp 23a and the second clamp 23b holding the sample housing 101 move together in one direction. However, in an embodiment not shown herein, the first clamp and the second clamp can move independently from each other.

Also shown in FIG. 3a are sensor means 25 on the first clamp 23a for detecting contact of the first clamp 23a and the sample housing 101. In another not shown embodiment, both the first and second clamp could comprise sensor means.

For demolding, the blade 13 associated with the actuation means 17 moves over the surface of the sample housing 101 to get hold of at least part of the closing means 105 and to remove it from the sample housing 101 while the blade 13 moves into the second position as shown in the following figures. The demolding means 11 also comprises a supporting surface 15 on which at least part of the cover plate 103 rests on prior to demolding in the first position of the actuation means 17.

Figure 3C:
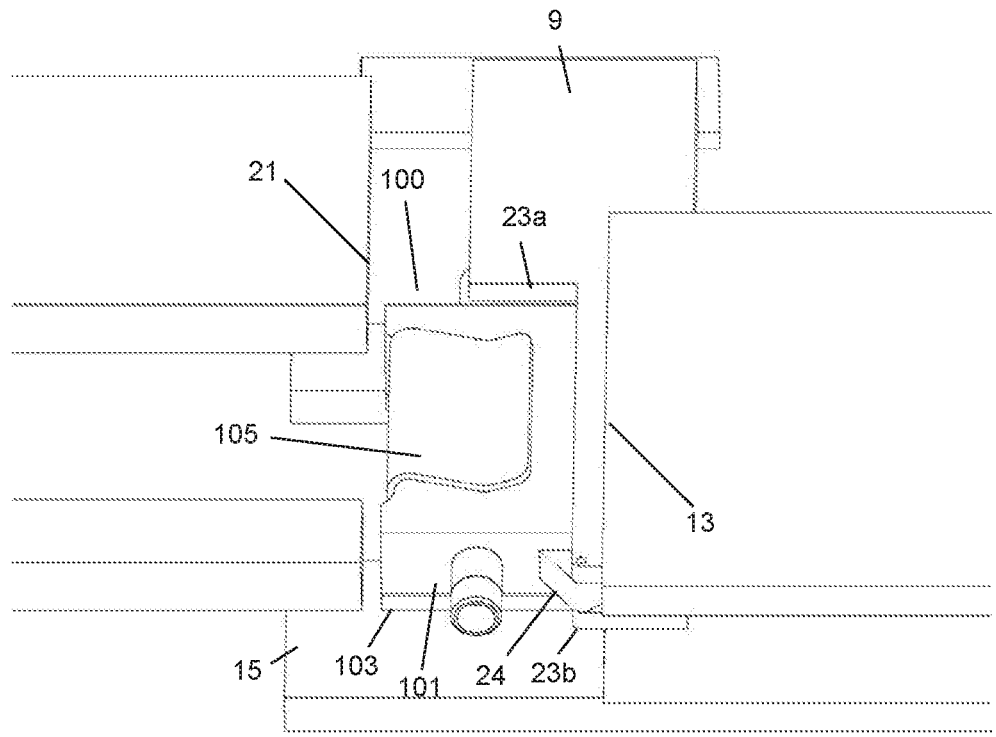
Figure 3D:
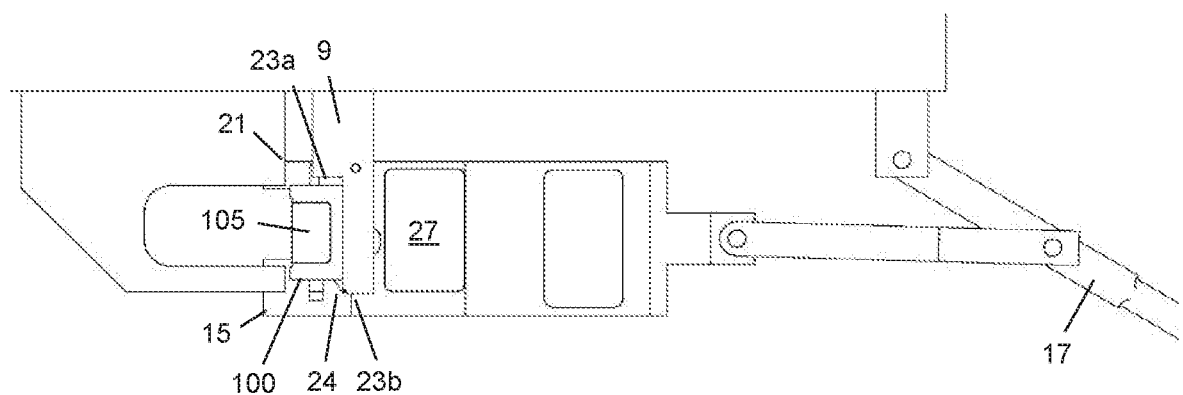

When the actuation means 17 moves from the first position into the second position, the supporting surface 15 moves away from the cover plate 103 so that the cover plate 103 can separate from the sample housing 101 by means of gravitational force and can drop through an aperture 27, which can be best seen in FIG. 3d, arranged next to the supporting surface 15 to expose the analysis surface of the sample. In the shown embodiment removing the closing means 105 and moving away the supporting surface 15 takes place in a sequential order.

FIG. 3b shows a schematic top view of the transporting means 9 and the demolding means 11 with the actuation means 17 in the first position. In addition to the components already shown in the previous figure, an abutment surface 21 and the collection bin 19 for collecting the removed closing means 105 and cover plate 103 are depicted. The abutment surface 21 is arranged to prevent movement of the sample housing 101 in the sideways direction during demolding. However, the abutment surface 21 is merely optional, since the first clamp 23a and the second clamp 23b can be designed to prevent movement of the sample housing 101 in the forward/backward and sideways direction during demolding.

In an example, the transporting means 9 comprises the abutment surface 21 arranged at least in part parallel to the second clamp 23b to prevent movement of the sample housing 101 in a sideways direction by wedging the sample housing 101 between the abutment surface 21 and the first clamp 23a and second clamp 23b. The abutment surface 21 can be rigidly arranged, for example on the cabinet, relative to the demolding means 11, wherein the distance between abutment surface 21 and the first and/or second clamp 23a, 23b can be chosen to match the width of the sample housing 101.

FIGS. 3c and 3d show an embodiment of the invention, where the second clamp 23b comprises locking means 24 realized by a spring biased latch which allows the sample housing 101 to be moved past the locking means 24 towards the first clamp 23a for inserting the direct analysis sample into the apparatus. Once the sample housing 101 was moved past the locking means 24, the locking means 24 prevents movement of the sample housing 101 in the opposite direction, i.e. in a direction away from the first clamp 23a. Also, as shown in FIG. 3d, the aperture 27 is an aperture, throughhole, or passage opening in the material of the supporting surface 15 which is dimensioned to allow the cover plate to fall through.

Figure 4:
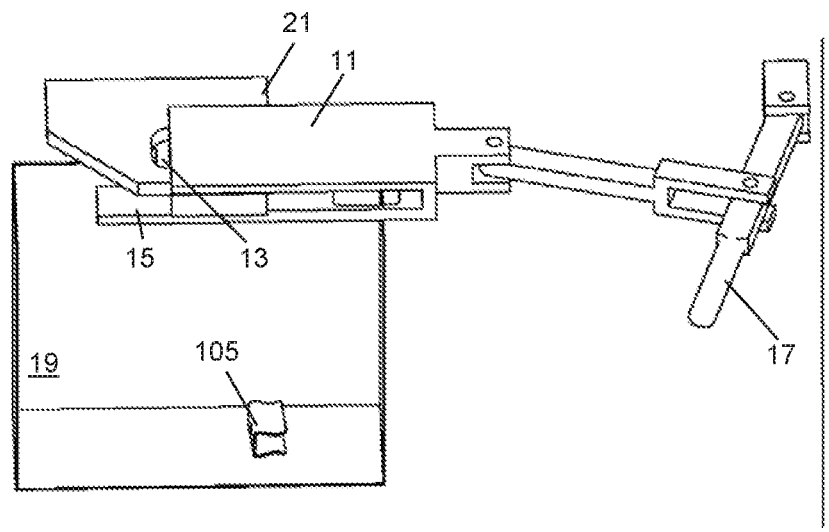
FIG. 4 shows a schematic view of the demolding means with the actuation means between the first position and a second position according to an embodiment of the invention.
Figure 5:
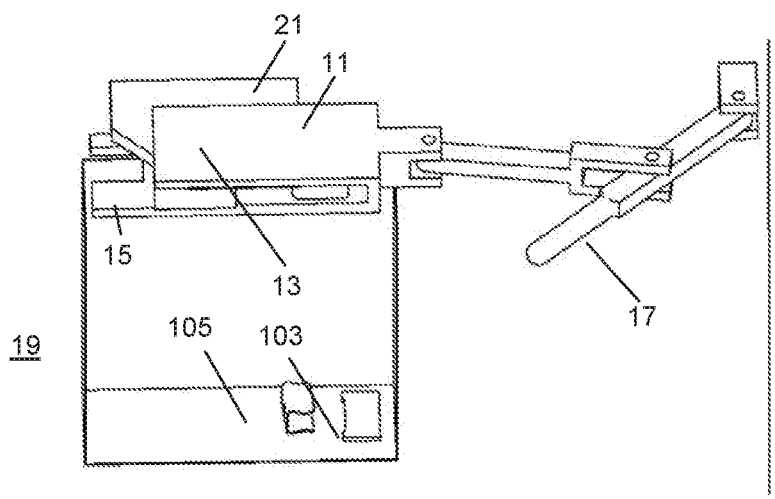
FIG. 5 shows a schematic view of the demolding means with the actuation means in the second position according to an embodiment of the invention.

FIG. 4 shows a schematic view of the demolding means 11 with the actuation means 17 between the first position and a second position according to an embodiment of the invention. As already described with reference to FIGS. 3a-3d, the demolding can take place sequentially, where the blade 13 removes the closing means 105 from the sample housing 101 in a first step. When the actuation means 17 is moved further towards the second position, the supporting surface 15 is not any longer supporting the cover plate 103. So, the cover plate 103 separates from the sample housing 101 and drops through the aperture, shown in FIG. 3d, into the collection bin 19 shown in FIG. 5.

Figure 6A:
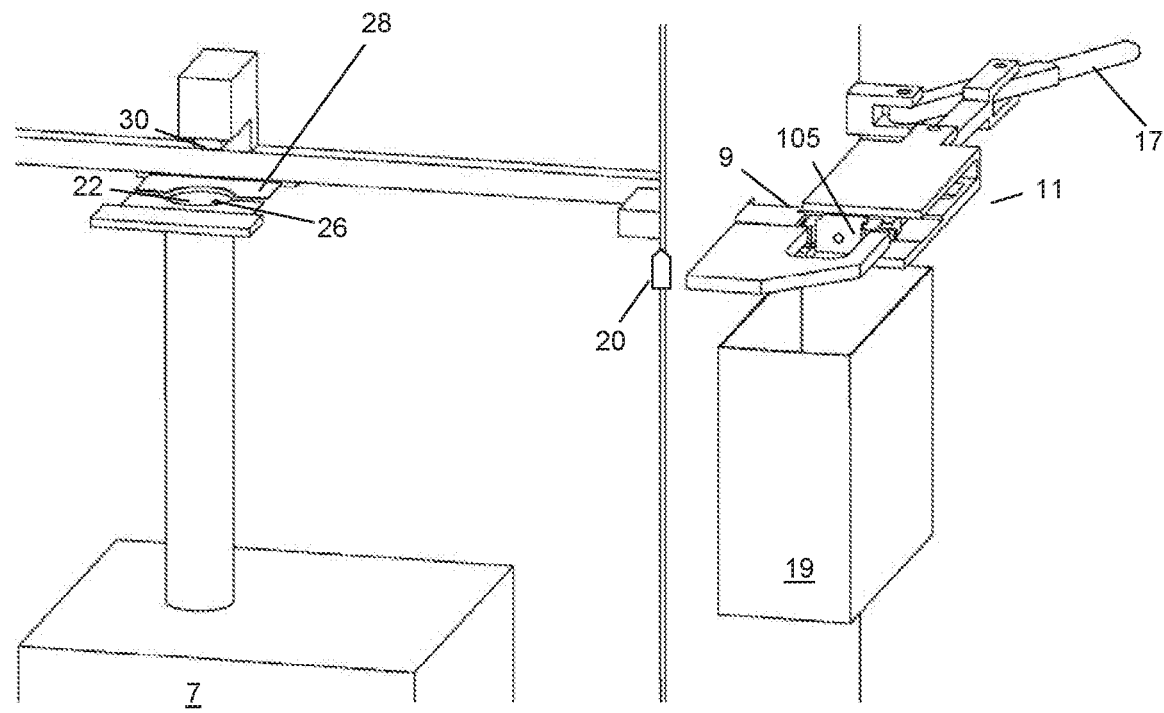
FIGS. 6a-6d show schematic views of the transporting means, the demolding means, and the analysis means according to an embodiment of the invention.
Figure 6B:
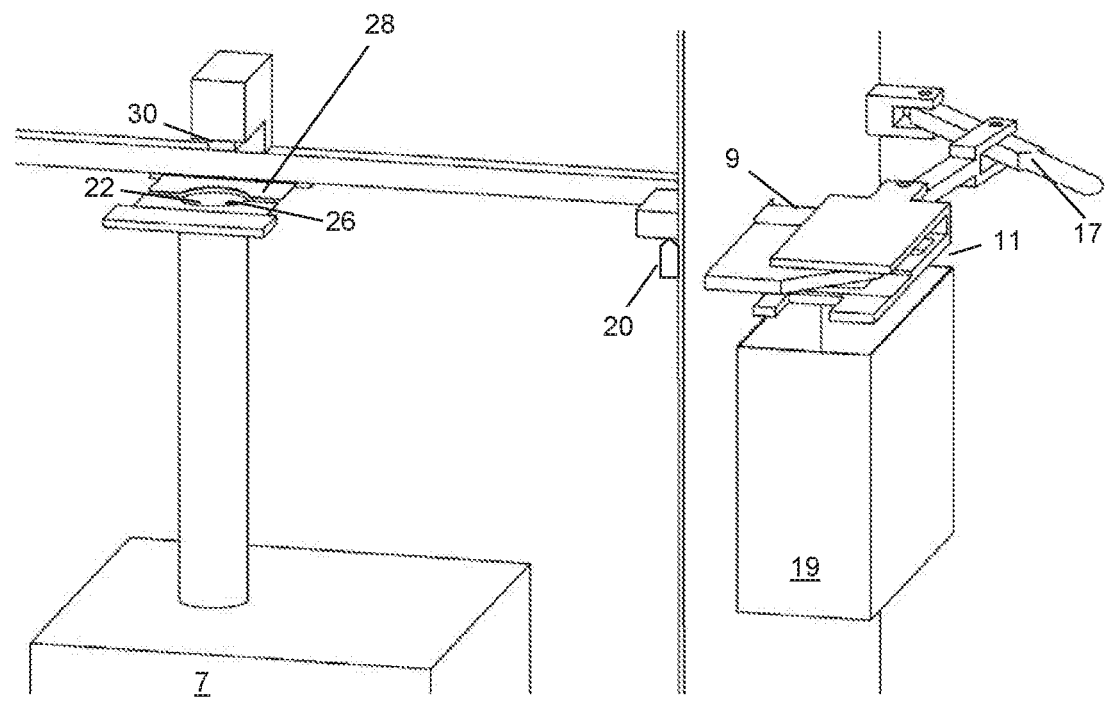

FIGS. 6a-6d show schematic views of the transporting means 9, the demolding means 11, and the analysis means 7 according to an embodiment of the invention. In FIG. 6a, the demolding means 11 is in the first position as already shown in FIGS. 3a and 3b. The transporting means 9 is in the demolding position to allow the demolding means 11 to remove the closing means 105 and to expose the analysis surface of the sample. FIG. 6b shows the demolding means 11 in the second position as already shown in FIG. 5. The analysis surface of the sample (not shown) is now exposed and is ready for transport from the demolding position into the analysis position along an axis extending from a sample bay, where the sample is inserted (which can be the demolding position) to the analysis means/analysis position.

In the shown embodiment, the demolding position is the same position as an inserting position where the sample is inserted into the transporting means 9. In an alternative embodiment (not shown in here), the demolding position and the inserting position can be different positions where the sample is transported between the inserting position, the demolding position, and the analysis position.

Figure 6C:
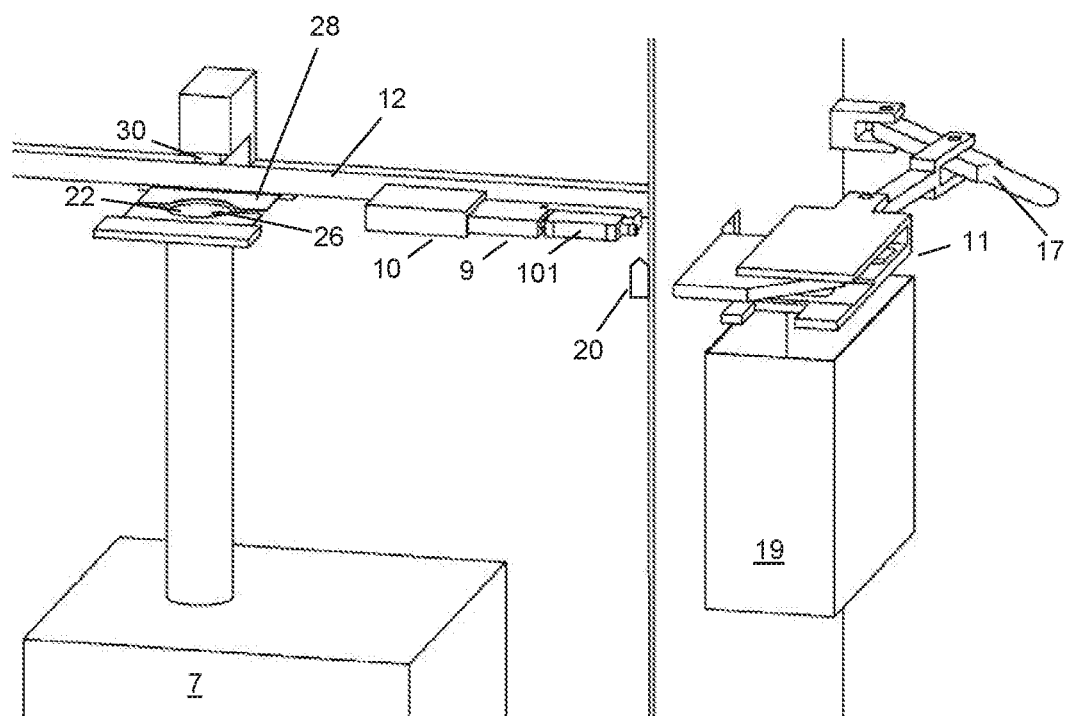

FIG. 6c shows the transport of the sample housing 101 from the demolding position into the analysis position. As depicted, the sample housing 101 is transported having its analysis surface directed towards a contact electrode of the analysis means 7, which comprises in the shown embodiment an optical emission spectrometer, while being held by the transporting means 9. For transporting the sample housing 101, the transporting means 9 comprises drive means 10 such as an electric motor, a pneumatic drive, or a manual drive to move the transporting means 9 on a slider system 12 such as the shown glide surface/track or slide cam between the demolding position and the analysis position. For example, a position sensor connected to a controlling unit (both position sensor and controlling unit are not shown in FIGS. 6a-6c) can detect that the actuation means 17 was brought into the second position, which triggers the controlling unit to activate the drive means 10. As it can be seen, the sample housing 101 is transported with the analysis surface of the sample spaced from surrounding objects such that the analysis surface of the sample is held and transported contact, abrasion and/or friction free.

In the shown embodiment the apparatus also comprises means to apply purge gas 20 to the analysis surface of the sample for removing loosely attached particles. The means to apply purge gas 20 comprise a gas nozzle arranged between the demolding position and the analysis position. As shown, the gas nozzle is arranged inside the cabinet at the opening for the sample housing 101 to enter the cabinet and is adapted to apply a short gas purge to the analysis surface of the sample when the sample housing 101 is moved past the gas nozzle to remove loosely attached particles from the analysis surface.

Figure 6D:
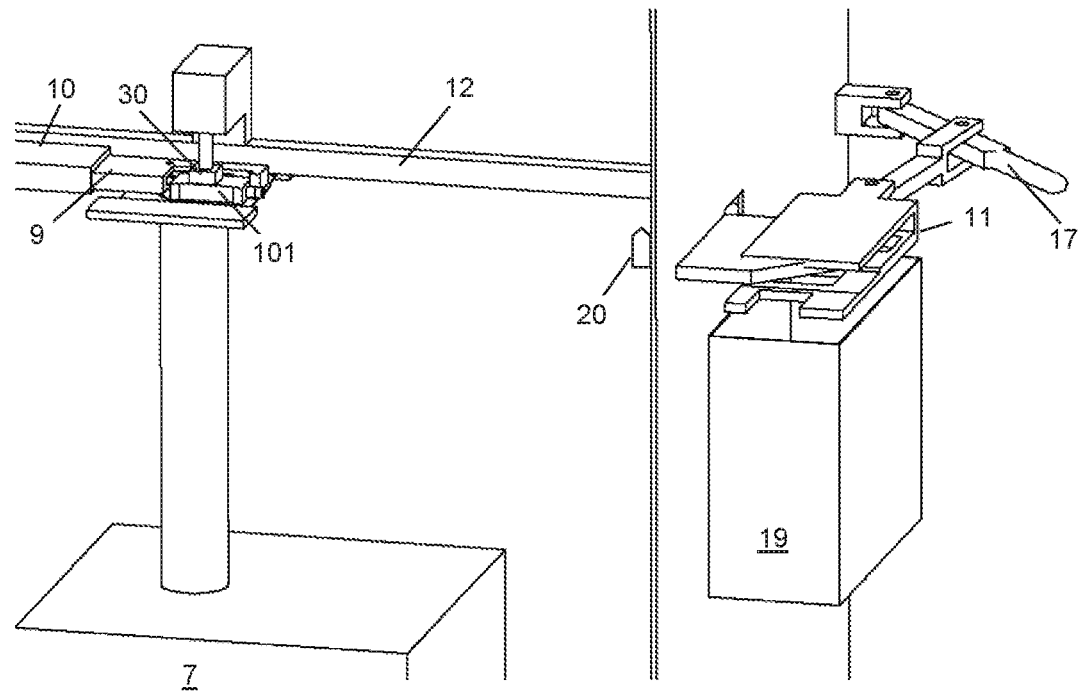

Once the transporting means 9 has arrived in the analysis position, as shown in FIG. 6d, the controlling unit can trigger the analysis means 7 to analyze the analysis surface of the sample.

In the embodiment shown in FIGS. 6a-6d, the analysis means 7 comprises a top-loaded optical emission spectrometer comprising a spring 28 to hold the analysis surface of the sample at a distance to a contact electrode 26 of the optical emission spectrometer, and which is adapted to establish an electric contact to the analysis surface of the sample when the spring 28 is in a compressed state.

The spring 28 has a spring force sufficiently high to push the sample housing 101 containing the sample away from a contact surface 22 of the optical emission spectrometer. This allows to re-arrange the analysis surface on the contact surface 22 for moving the sample to different analysis spots on the analysis surface for a plurality of analysis or just one more analysis after the first analysis was done. The shown setting prevents contact of the analysis surface of the sample with materials that might contaminate the analysis surface. FIGS. 6a-6d also show that the optical emission spectrometer comprises a push rod 30 to push the sample housing 101 with the analysis surface first onto the contact surface 22 of the optical emission spectrometer to establish an electrical contact between the analysis surface and the contact electrode 26.

Figure 7A:
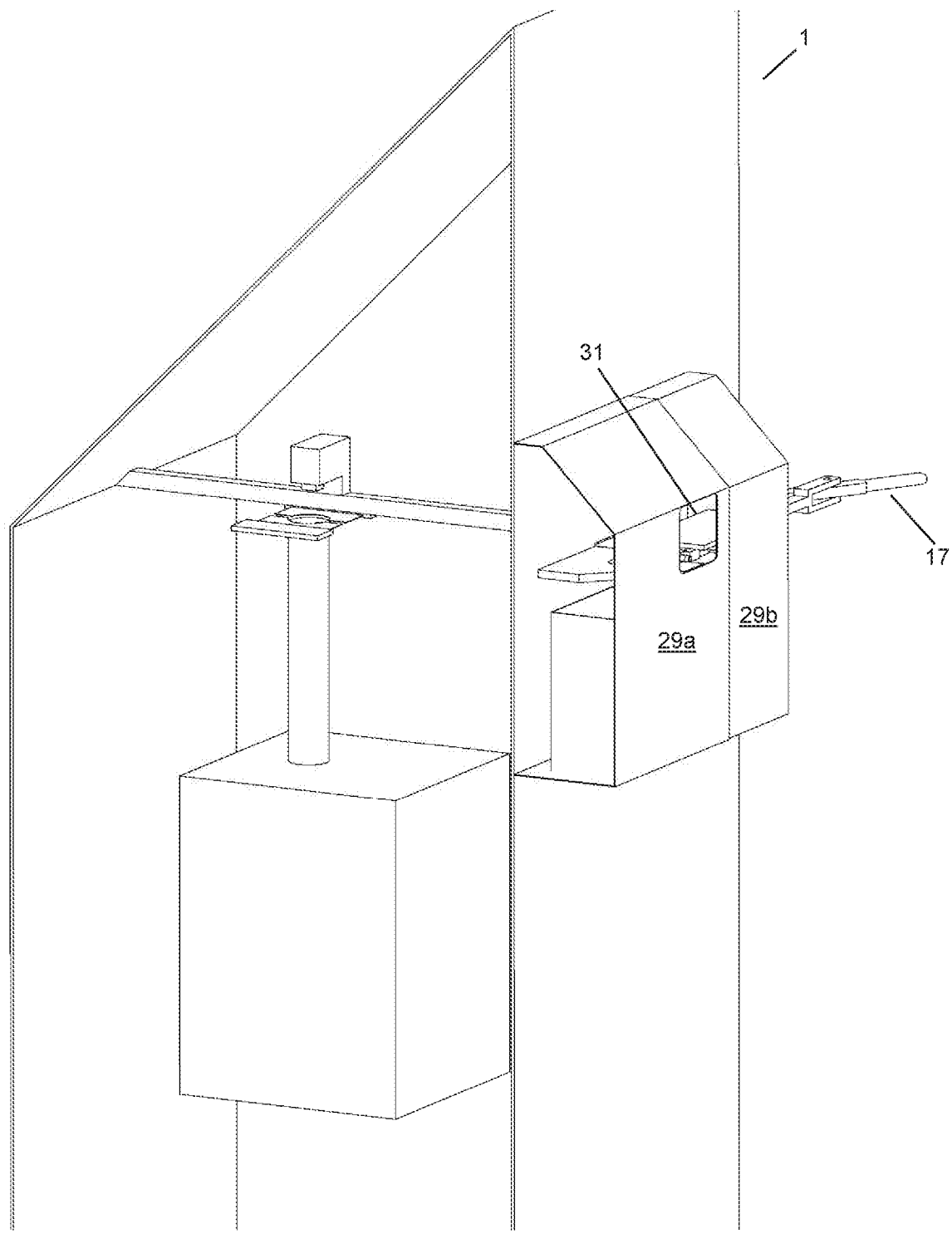
FIGS. 7a, 7b show schematic views of an apparatus for demolding and analyzing a direct analysis sample comprising a first dust cover and a second dust cover according to an embodiment of the invention.
Figure 7B:
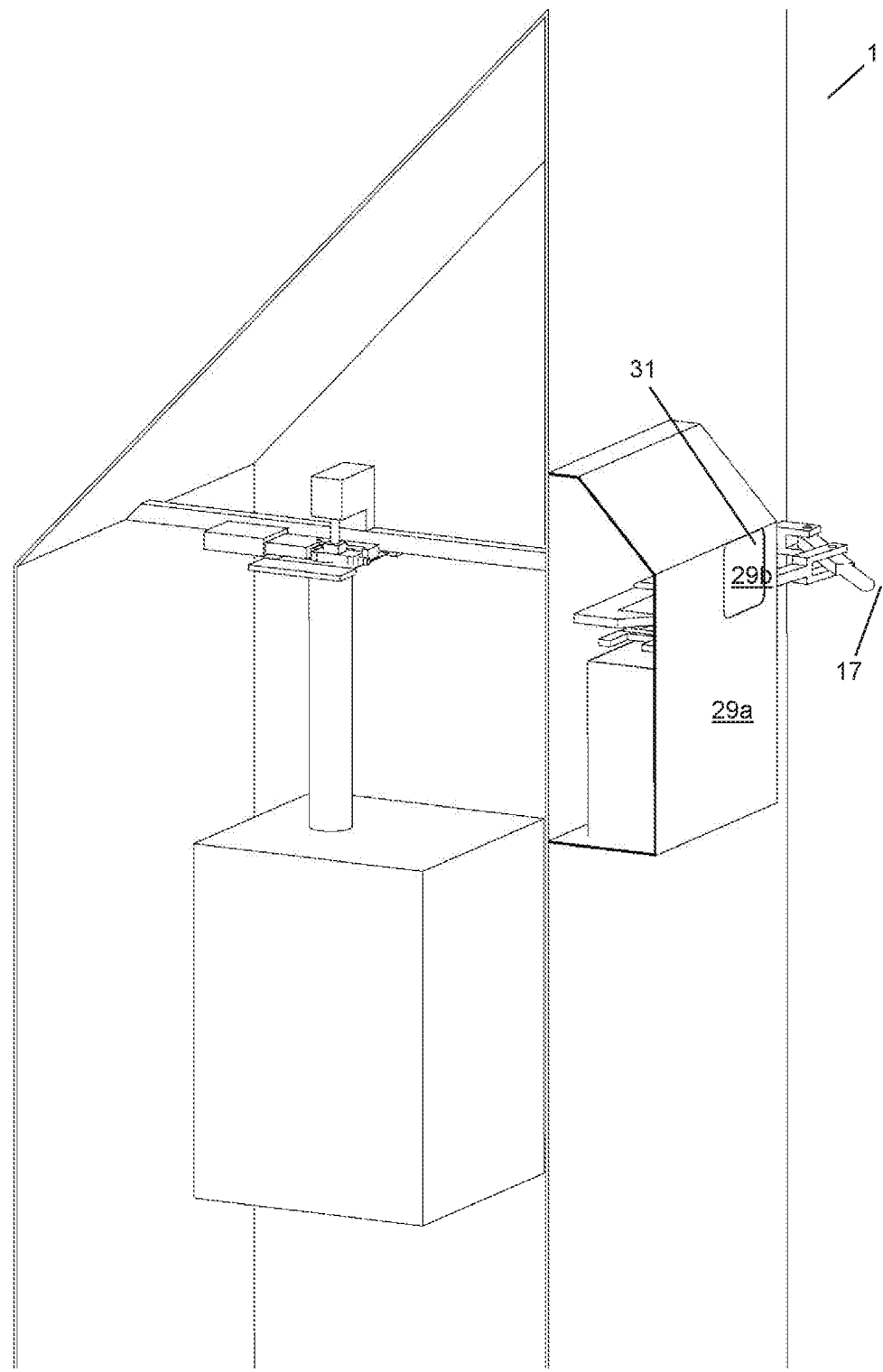

FIGS. 7a and 7b show schematic views of an apparatus 1 for demolding and analyzing a direct analysis sample comprising a first dust cover 29a and a second dust cover 29b according to an embodiment of the invention.

In the shown embodiment, the first dust cover 29a is mounted on a stationary part of the apparatus 1, and the second dust cover 29b is mounted on the blade or on a movable part mechanically associated with the blade and moving together with the blade when the actuation means is 17 is moved from the first position into the second position and vice versa. The first dust cover 29a comprises an insertion-opening 31 for inserting the sample chamber assembly into the transporting means. As shown in FIG. 7b, the second dust cover 29b overlaps the insertion-opening 31 when the actuation means 17 is in the second position.

The features disclosed in the claims, the specification, and the drawings may be essential for different embodiments of the claimed invention, both separately or in any combination with each other.

REFERENCE SIGNS

1 Apparatus for Demolding and Analyzing
3 Cabinet
5 Opening
7 Analyzing Means
9 Transporting Means
10 Drive Means
11 Demolding Means
12 Slider System
13 Blade
15 Supporting Surface
17 Actuation Means
19 Collection Bin
20 Means to Apply Purge Gas
21 Abutment Surface
22 Contact Surface
23a, 23b First Clamp, Second Clamp
24 Locking Means
25 Sensor Means
26 Contact Electrode
27 Aperture
28 Spring
29a, 29b first Dust Cover, Second Dust Cover
30 Push Rod
31 Insertion Opening
100 Sample Chamber Assembly
101 Sample Housing
103 Cover Plate
105 Closing Means 107 Sample Cavity
109 Analysis Surface

The invention claimed is:

1. An apparatus for demolding and analyzing a direct analysis sample formed within a sample chamber assembly from a molten metal material, wherein the sample chamber assembly comprises a sample housing, a cover plate, and a closing mechanism holding the sample housing and the cover plate together, the apparatus comprising:
 a cabinet defining an interior and comprising at least one opening for the sample housing to enter the cabinet, and a sample analyzer located inside the cabinet for analyzing an analysis surface of the direct analysis sample;
 a demolding mechanism adapted to engage the closing mechanism and to remove at least the closing mechanism from the sample housing and the cover plate to expose at least part of the analysis surface of the direct analysis sample; and
 a transporting mechanism adapted to hold and transport the sample housing at least between a sample demolding position, where the closing mechanism is removed from the sample chamber assembly by the demolding mechanism, and a sample analysis position, where the analysis surface of the sample contained within the sample housing is analyzed by the sample analyzer, and wherein the sample demolding position and the sample analysis position are different from each other.

2. The apparatus of claim 1, wherein the demolding mechanism comprises at least one blade arranged in at least a sideways direction or a longitudinal direction relative to an axis formed by the demolding position and the analysis position and adapted:
 (i) to move over a surface of the sample chamber assembly to remove the closing mechanism from the sample chamber assembly, or
 (ii) to move over a surface of the sample chamber assembly to remove the closing mechanism and to penetrate the sample chamber assembly to expose at least part of the analysis surface of the sample.

3. The apparatus of claim 2, wherein the demolding mechanism further comprises an actuation means for moving the at least one blade and the at least one supporting surface, and wherein the actuation means comprises a hand gear for moving the at least one blade and the supporting surface mechanically, or a push rod for moving the at least one blade and the at least one supporting surface pneumatically or electrically, between a first position and a second position.

4. The apparatus of claim 3, wherein the transporting mechanism comprises:
 a first clamp and a second clamp for holding the sample housing and to stop movement of the sample housing in at least a forward direction and a backward direction from both the demolding position and the sample analysis position, wherein the first clamp and the second clamp are movably arranged in the forward and the backward direction for transporting the sample housing between the sample demolding position and the sample analysis position, wherein the second clamp is arranged at least in part opposite the first clamp, and
 wherein the actuation means is adapted to be moved between the first position and the second position, wherein:
  in the first position, the actuation means and the at least one blade are arranged for loading the sample housing, wherein at least the first clamp is at least partly arranged in the opening of the cabinet, and
  in the second position, the actuation means and the at least one blade are arranged for analyzing the sample by the sample analyzer, wherein at least the second clamp is at least partly arranged in the opening of the cabinet.

5. The apparatus of claim 4, further comprising:
 at least a first dust cover mounted on a stationary part of the apparatus, and a second dust cover mounted on the blade or a moveable part mechanically associated with the blade and moving together with the blade, wherein at least part of the first dust cover and the second dust cover are arranged to be spaced apart to allow loading the sample chamber assembly when the actuation means is in the first position, and at least partly overlap when the actuation means is in the second position.

6. The apparatus of claim 5, wherein the first dust cover comprises an insertion-opening for inserting the sample chamber assembly into the transporting mechanism, and wherein the second dust cover overlaps the insertion-opening when the actuation means is in the second position.

7. The apparatus of claim 5, further comprising at least one dust seal arranged the first dust cover and/or the second dust cover to seal a remaining space between the first dust cover and the second dust cover when they are overlapping.

8. The apparatus of claim 2, wherein the closing mechanism is a clamp.

9. The apparatus of claim 1, wherein the demolding mechanism further comprises at least one supporting surface to support at least a part of the cover plate of the sample chamber assembly when held by the transporting mechanism, and wherein the at least one supporting surface is movably arranged to allow the cover plate to separate from the sample housing by means of gravitational force.

10. The apparatus of claim 1, wherein the transporting mechanism comprises:
 a first clamp and a second clamp for holding the sample housing and to stop movement of the sample housing in at least a forward direction and a backward direction from both the demolding position and the sample analysis position, wherein the first clamp and the second clamp are movably arranged in the forward and the backward direction for transporting the sample housing between the sample demolding position and the sample analysis position, wherein the second clamp is arranged at least in part opposite the first clamp.

11. The apparatus of claim 10, wherein the first clamp or the second clamp further comprises a sensor means for detecting contact of the first clamp or the second clamp and the sample housing.

12. The apparatus of claim 10, wherein
 the second clamp comprises a first locking means adapted to allow the sample housing to be moved past the first locking means towards the first clamp, and to prevent movement of the sample housing in an opposite direction, and
 the first clamp comprises a second locking means adapted to prevent movement of the sample housing in the forward direction and backward direction.

13. The apparatus of claim 1, wherein the sample analyzer comprises an optical emission spectrometer.

14. The apparatus of claim 13, wherein the optical emission spectrometer is
 (i) a spark optical emission spectrometer, or
 (ii) a top-loaded optical emission spectrometer comprising a spring to hold the analysis surface of the sample at a distance to a contact electrode of the top-loaded optical emission spectrometer, and adapted to establish an electric contact to the analysis surface of the sample when the spring is in a compressed state.

15. The apparatus of claim 14, wherein the spring has a force of less than 100 Newton, to hold the analysis surface at a distance of less than 1 mm to the contact electrode of the top-loaded optical emission spectrometer.

16. A system for demolding and analyzing a direct analysis sample comprising:
    an apparatus according to claim 1; and
    a direct analysis sample formed from a molten metal material contained within the sample chamber assembly, wherein a ratio of a mass of the sample housing to a mass of the molten metal material solidified in the sample housing is higher than 5.

17. A method for demolding and analyzing a direct analysis sample formed within a sample chamber assembly from a molten metal material, wherein the sample chamber assembly comprises a sample housing, a cover plate and a closing mechanism holding the sample housing and the cover plate together, the method comprising:
    holding and transporting the sample housing at least between a sample demolding position and an analyzing position, wherein the sample demolding position and the analyzing position are different from each other;
    engaging the closing mechanism with a demolding mechanism and removing the closing mechanism from the sample housing and the cover plate with the demolding mechanism to expose at least part of an analysis surface of the direct analysis sample in the sample demolding position; and
    analyzing the analysis surface of the direct analysis sample in the analyzing position with a sample analyzer located inside a cabinet after transporting the sample housing from the demolding position through an opening in the cabinet into the analyzing position.

18. The method of claim 17, wherein holding and transporting comprises:
    holding the sample housing between a first clamp and a second clamp to stop movement of the sample housing in at least a forward direction and a backward direction.

19. The method of claim 18, wherein removing the closing mechanism comprises:
    moving at least one moveably arranged blade in at least a sideways direction or a longitudinal direction relative to the first and second clamp:
    (i) over a surface of the sample chamber assembly to remove the closing mechanism of the sample chamber assembly holding the sample housing and the cover plate together, or
    (ii) over a surface of the sample chamber assembly to remove the closing mechanism and to penetrate the sample chamber assembly to remove the cover plate from the sample housing, to expose at least part of the analysis surface of the sample, and
    moving a supporting surface in at least the sideways direction to allow the cover plate to separate from the sample housing by means of gravitational force.

20. The method of claim 17, wherein holding and transporting the sample housing comprises:
    holding and transporting the sample housing, after removing the closing mechanism and cover plate, with the analysis surface of the sample spaced from surrounding objects such that the analysis surface of the sample is held and transported contact, abrasion and/or friction free.

* * * * *